United States Patent [19]

Yoshida

[11] Patent Number: 5,467,125
[45] Date of Patent: Nov. 14, 1995

[54] APPARATUS FOR THE INSPECTION OF TRANSPARENT CONTAINERS

[75] Inventor: Hajime Yoshida, Tokyo, Japan

[73] Assignee: Hajime Industries Ltd., Tokyo, Japan

[21] Appl. No.: 317,681

[22] Filed: Oct. 5, 1994

Related U.S. Application Data

[63] Continuation of Ser. No. 95,822, Jul. 21, 1993, abandoned, which is a continuation of Ser. No. 728,511, Jul. 11, 1991, abandoned.

[30] Foreign Application Priority Data

Jul. 13, 1990 [JP] Japan ................................. 2-185667

[51] Int. Cl.$^6$ ................................................. H04N 7/18
[52] U.S. Cl. ............................. 348/127; 348/125; 348/86
[58] Field of Search .......................... 348/87, 88, 89, 348/125, 127; 356/239, 240

[56] References Cited

U.S. PATENT DOCUMENTS

| | | | |
|---|---|---|---|
| 4,305,658 | 12/1981 | Yoshida | 356/108 |
| 4,459,023 | 7/1984 | Reich et al. | 356/240 |
| 4,580,045 | 4/1986 | Kulig | 356/240 |
| 4,644,151 | 2/1984 | Juvinall | 356/240 |
| 5,091,963 | 2/1992 | Litt et al. | 358/106 |

FOREIGN PATENT DOCUMENTS 0302146  12/1989  Japan ................................. 358/106

*Primary Examiner*—Curtis Kuntz
*Assistant Examiner*—Minsun Oh
*Attorney, Agent, or Firm*—Bauer & Schaffer

[57] ABSTRACT

A light source irradiates one side of a transparent container and a video camera is placed to pick up the image of the transparent container so that it will not directly receive the reflection of light from the light source. A nonreflecting plate is placed behind the container in opposition to the video camera. An image processor processes the output image of the camera. A light diffusion plate may be placed in front of the light source.

4 Claims, 2 Drawing Sheets

APPARATUS FOR THE INSPECTION OF TRANSPARENT CONTAINERS

This is a Continuation of Ser. No. 08/095,822, filed Jul. 21, 1993, now abandoned, which is a Continuation of Ser. No. 07/728,511, filed Jul. 11, 1991, now abandoned.

BACKGROUND OF THE INVENTION

1. Field of the Invention

The present invention relates generally to inspection apparatus and, more particularly, is directed to a bottle or container inspection apparatus that detects a flaw such as a blowhole, blister or the like existing in the wall of a transparent type container.

2. Description of the Prior Art

In the recent years, plastic containers that are made of plastic materials such as polyethylene, etc., have become used as preservation containers for liquors, beverages or seasonings by substituting glass containers. Such containers feature easier massproduction, and are light weight and lower costing with the additional merit that breakage cautions like in the case of glass bottle are not necessary. However, a precaution point upon producing such containers is the prevention of flaws such as blowhole, blister, bubbles or the like flaw within the container wall.

Plastic containers are mainly produced by blow moulding methods whereas cases that air bubbles get mixed into the material may be relatively high. By moulding containers with materials containing air bubbles or by the mixture of air bubbles into the material during the moulding process, the formed product or container will carry a residual air bubble that is thinly compressed into its walls which are apt to cause the wall tear or damage at such wall portion with blister during usage or transit.

The detection of such extremely thin and minute blister existence within the container's thin wall can be a very difficult task by the human vision.

FIG. 1 schematically shows one example of the main portions of a blister inspection apparatus according to the conventional art. In this example, the light from a light source 1 is irradiated onto a container 3 via a light diffuser plate 2, whereas a video camera 4 at the opposite side of container 3 in relation to the light source 1, receiver the light passing through the container, and then the video signal from the camera 4 is processed to inspect the existence or not of defects in the container 3.

However, in relations to the blisters within the container 3 walls, the contrast difference of brightness between the portions containing the blisters and none is extremely subtle to an extent that it was impossible to steadily and positively detect blister extistences by the conventional apparatuses.

In other wards, with the conventional inspection apparatus, while it was possible to detect the exsistences of opaque foreign particle such as stones or the like in the walls of container 3, it was very difficult to detect the existence of minute blisters within the walls. Further, by attempts to detect the existence of such minute blisters within the walls, since the contrast difference is subtle as mentioned above, at the conventional apparatus, it required complex image processing in order to boost such contrast difference. Further, it is incidental to such measure that the S/N (Signal to Noise) ratio detoriorates to an extent that the blister detection lacks stability so that the practical status was that such apparatus were not suitable for actual use.

OBJECTS AND SUMMARY OF THE INVENTION

Accordingly, it is an object of the present invention to provide an improved transparent container inspection apparatus which can obviate the short commings encoutered with the prior art.

According to the present invention, there is provided a transparent container inspection apparatus comprising:

a) a light source for irradiating a transparent container from its one side;

b) a video camera placed so that it will not directly receive the irradiated light from said light source and for picking up an image of said container;

c) an image processor for processing the output image signal from said video camera; and d) a non-light reflection plate placed at the counter side of said video camera with respect to said container.

According to another aspect of the present invention, there is provided a transparent container inspection apparatus comprising:

a) a light source for irradiating a transparent container from its one side;

b) a light diffusion plate located in front of said light source;

c) a video camera placed so that it will not directly receive the irradiated light from said light source and for picking up an image of said container;

d) an image processor for processing the output image signal from said video camera; and e) a non-light reflection plate placed at the counter side of said video camera with respect to said container.

BRIEF DESCRIPTION OF THE DRAWINGS

A better understanding of the objects, features and advantages of the invention can be gained from a consideration of the following detailed description of the preferred embodiments thereof, in conjunction with figures of the accompanying drawings, wherein.

DETAILED DESCRIPTION OF THE PREFERRED EMBODIMENT

An embodiment of the transparent container inspection apparatus according to the present invention will be explained hereunder in reference with the drawings.

Figure 2A:
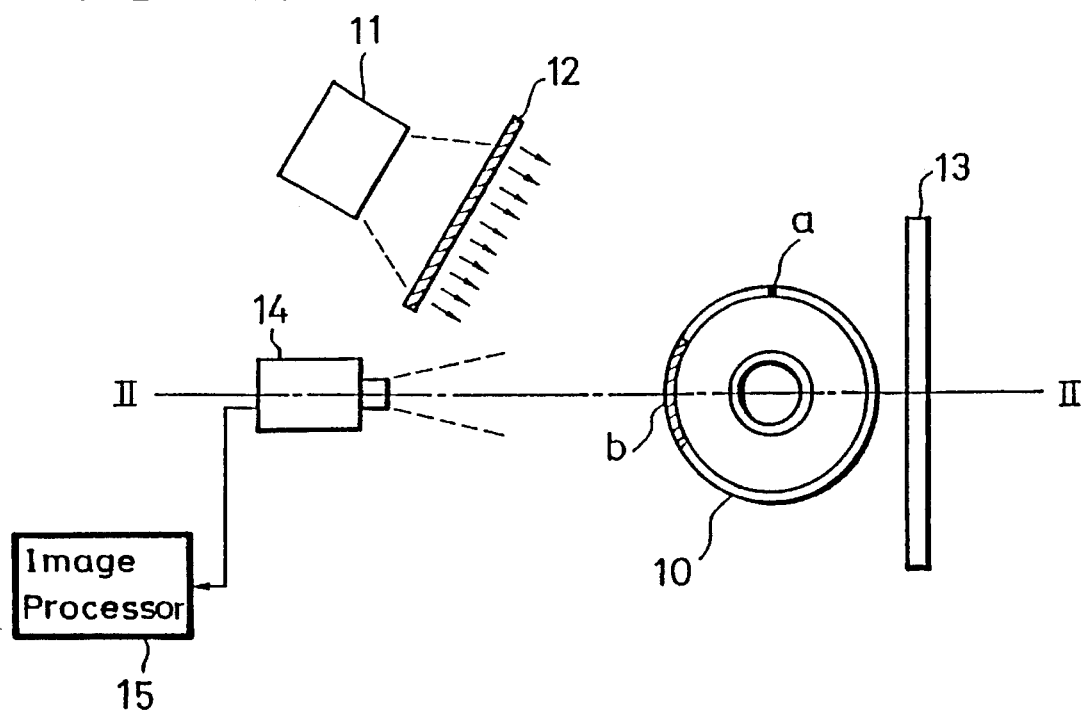
FIG. 2A is a schematic top view showing an embodiment of the present invention.
Figure 2B:
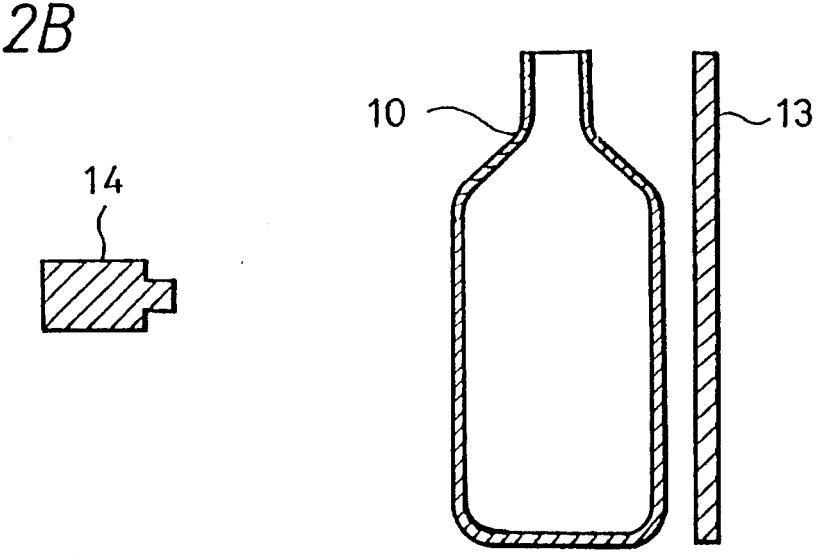
FIG. 2B is a cross sectional diagram along the line II—II in FIG. 2A.

FIG. 2A is a schematic top view showing an embodiment of the present invention, and FIG. 2B is a cross-sectional view along the line II—II in FIG. 2A.

In FIG. 2, 10 is a container to be inspected, made of transparent material such as transparent plastic material or the like. 11 is a light source that irradiates upon container 10 which in this example irradiates upon container 10 uniformly from one side through a light diffusion plate 12. At the counter side to the light source 11 with respect to the container 10, a non-light reflection plate 13 which does not reflect any lights and is sufficiently larger than the container 10 in area is placed along container 10. 14 is such as a video camera which is placed at the same side of the light source 11 relative to the container 10 in order to pick up an image of the container 10, whereas it is arranged so that the light from the light source 11 does not directly eater the video camera 14. 15 is an image processor that is connected to video camera 14, which processes the image signals from the video camera 14 in order to inspect the existence or not of flaws such as blisters and so on in the container 10. In this embodiment, the non-light reflection plate 13 is formed by, for example, coating or adhesion of non-light reflection black paint or non-glossy paint or the like as well as textile, paper or other non-light reflection material on a substrate such as a plate made of plastics, wood, paper, metal and so on. In this case, it is preferred that the surface of the substrate is formed as a rough surface so that the above-mentioned point can be firmly addhesive to the surface of the substrate.

Next, the function of the example of the present invention as composed and placed as described above will be explained.

The visual field picked up by video camera 14 shall appear to be dark. That is to say, in general the irradiated light from the light source 11 that passes the transparent container 10 as well as the other light that do not pass the container 10 arrive at the non-light reflection plate 13 that does not reflect any light and hence are substantially absorbed thereat so that any lights do not enter the visual field of the video camera 14.

Apart from the above, in the case that blisters or the like are contained within the wall of the container 10, such blister will cause diffused reflection of the irradiated light thereto from the light source 11 so that only such diffused reflection light will arrive at and hence be picked up by the video camera 14. That is to say that within the dark vision of the video camera 14, the diffused reflection light from the blister will appear to be shining brightly. Therefore, by processing the output signal from video camera 14 at the processor 15, the blister detection is easily accomplished.

On the other hand, as shown by a on FIG. 2A, when the blister to be detected is at one side end of the container 10 against the visual field of video camera 14, there shall be occasions where the blister may appear difficult to be caught by the video camera 14 and accordingly, as shown on b of the same drawing it would be better to partially confine the inspection area of container 10 and rotate the container 10 so that its entire periphery will be inspected by several shots.

Figure 1:
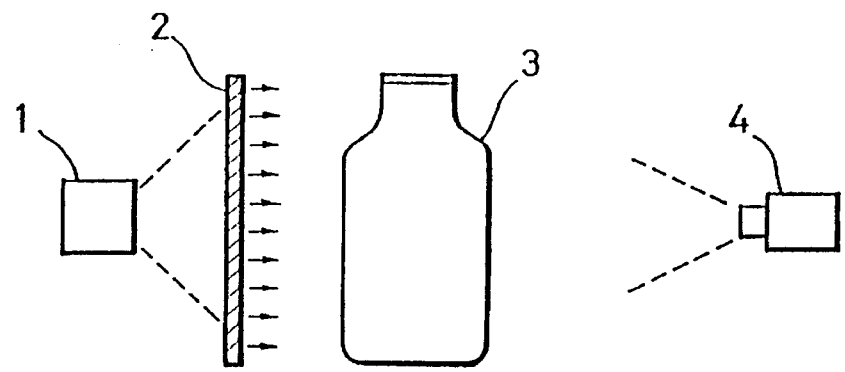
FIG. 1 is a schematic diagram showing an example of the conventional apparatus.
Figure 3A:
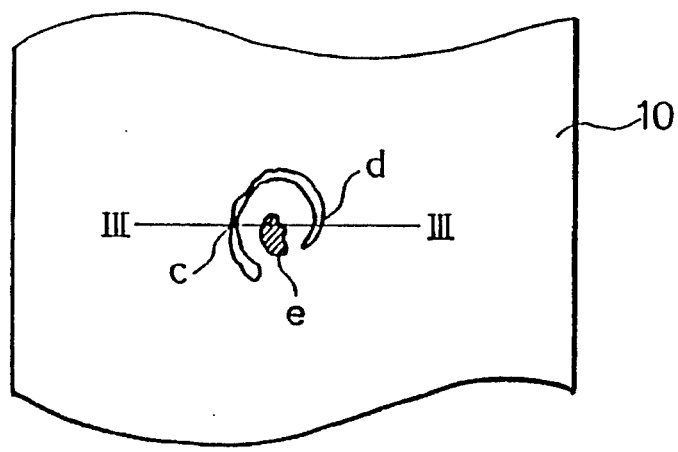
FIGS. 3(A–B) are schematic diagrams used for explaining the functions of the embodiment according to the present invention.
Figure 3B:
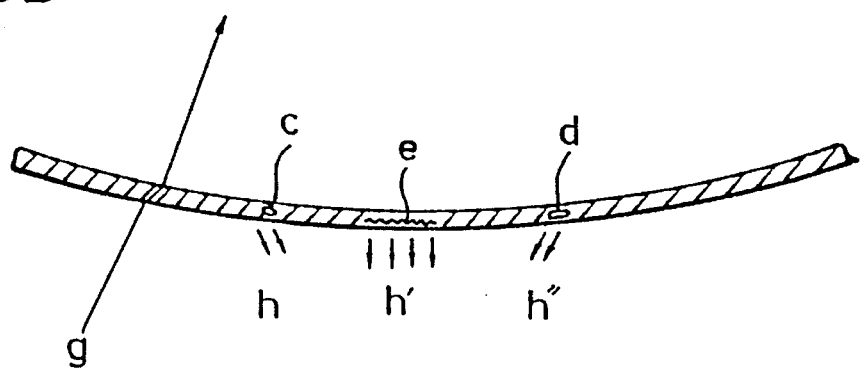

FIGS. 3A and 3B show an example of a blister residue within the container 10 wall, where FIG. 3A is the front view and FIG. 3B is an enlarged cross sectional view along the line III—III in FIG. 3A.

Blisters are generally compressed to take various forms when blow moulded and FIG. 3 shows a typical example taking a multi bubble type formation. However, no matter to which format such blister takes, the blister detection function of the present invention remains exactly the same so that the blister detection function by the present invention will be explained for the format as shown on FIG. 3.

FIG. 3A is a diagram that views the blister format from the front as facing the container 10 wall as above described, whereas in this example case, the blister that was compressed during the blow moulding formation of said container 10, draws arc shapes like c, d in thin strips about 1 cm in diameter as shown on same drawing. Also, a blister e that was at the center portion of such arc is the portion that could not escape towards the outer circumference.

As shown on FIG. 3B, amoung the light irradiated from the light source 11, the light that passes the container 10 wall where there are no blisters will not be reflected at the wall such as g and will proceed through the wall into container 10 inside. The light that has entered inside the container 10 will pass the wall at the opposite side to be absorbed by the non-light reflection plate 13 as shown on FIG. 2 and does not arrive at the video camera 14 as above described.

Contrarily, at blister portions c, d, e the irradiated light is diffuse-reflected to generate diffused reflection lights h, h', h" so that these diffused reflection lights h, h', h" arrive at and then are picked up by the video camera 14.

Thus, the video camera 14 picks up the diffused reflection lights from the blister group as bright images in a dark field so that such existence of blister group can be detected. Therefore, when in this case the output signal from the video camera 14 is processed by the image processor 15, it is easily and positively detected that the blisters exist in the wall of container 10.

Further, while the above explains the case of blister detection within the wall section of transparent containers by the apparatus of the present invention, but it is obvious that the apparatus of the present invention is capable of flaw detection other than blisters in the same manner.

Further, while plastic material was cited as the example of the transparent container material, it is needless to say that blister and flaws may be detected in the case that glass is used as the material of the container.

The present invention is a detection method that carries an entirely different concept to conventional inspection methods. That is to say that it makes it possible to maximize the contrast difference between the good portion (without any blisters) and the blister (flaw) within the image of the video camera 14 so that without necessitating a special and complex image processor system such blister extistence within the transparent container wall and so on can be simply detected.

Further, it is mentioned that in addition to a simple image processor being sufficient by the present invention, extremely minute blisters can be positively detected so that a low costing inspection apparatus can be presented. Also, the entire inspection apparatus composition is not complicated and can be simply installed which makes practical adaptation very simple.

It should be understood that the above description is presented by way of example on the preferred embodiment of the invention and it will be apparent that many modifications and variations thereof could be effected by one with ordinary skill in the art without departing from the spirit and scope of the novel concepts of the invention so that the scope of the invention should be determined only by the appended claims.

I claim as my invention:

1. Apparatus for inspecting light transparent containers comprising a source of light, a light diffuser interposed between said light source and said container to irradiate said container uniformly, and a video camera, said source of light, said light diffuser and said video camera being arranged to have a field of irradiation and a field of view respectively from the same side of said container and through said container, a light absorbing wall placed behind said container in opposition to said video camera and in line to absorb the light passing through said container, said source of light, said light diffuser and said video camera being further arranged relative to each other so that light irradiated on the surface of said container is not reflected therefrom but passes through said container, and hence, said video camera receives only spurious reflection from said container, and a processor for processing the output signal of said video camera upon the sensing of a spurious reflection from said container.

2. The transparent container inspection apparatus as claimed in claim 1, wherein said light absorbing wall comprises a plate formed of a substrate on the surface of which is coated black paint.

3. The transparent container inspection apparatus as claimed in claim 1, wherein said light absorbing wall comprises a plate formed of a substrate on the surface of which is painted non-glossy paint.

4. The transparent container inspection apparatus as claimed in claim 1, wherein the surface of said light absorbing wall is formed with a rough surface.

* * * * *